United States Patent [19]

Ebling

[11] 4,456,223

[45] Jun. 26, 1984

[54] FLOW CONTROL APPARATUS

[75] Inventor: Wendell V. Ebling, Placentia, Calif.

[73] Assignee: Bentley Laboratories, Inc., Irvine, Calif.

[21] Appl. No.: 327,111

[22] Filed: Dec. 3, 1981

[51] Int. Cl.³ .................................... F16K 31/524
[52] U.S. Cl. .............................. 251/342; 137/599; 137/DIG. 2; 604/33; 604/34; 604/249
[58] Field of Search ............... 604/30, 34, 83, 246, 604/250, 256, 33, 249; 137/DIG. 2, 599; 251/4, 117, 77, 80, 342

[56] References Cited

U.S. PATENT DOCUMENTS

| | | | |
|---|---|---|---|
| 1,099,032 | 6/1914 | Fraser | 137/DIG. 2 |
| 1,983,227 | 12/1934 | Hall et al. | 158/115 |
| 2,181,900 | 12/1939 | Langdon | 137/93 |
| 2,229,903 | 1/1941 | Schmohl et al. | 277/57 |
| 2,314,767 | 3/1943 | Burrell | 137/DIG. 2 |
| 2,706,101 | 4/1955 | Cantor | 251/4 |
| 2,964,292 | 12/1960 | Noir | 251/342 |
| 3,107,894 | 11/1963 | Quinn | 251/118 |
| 3,298,367 | 1/1967 | Bergman | 128/214 |
| 3,675,891 | 7/1972 | Reynolds | 251/117 |
| 3,840,207 | 10/1974 | Carpenter | 251/5 |
| 4,192,303 | 3/1980 | Young et al. | 128/214 |

FOREIGN PATENT DOCUMENTS

| | | | |
|---|---|---|---|
| 936438 | 11/1973 | Canada | 251/4 |
| 355675 | 6/1922 | Fed. Rep. of Germany | 251/4 |
| 1284219 | 11/1968 | Fed. Rep. of Germany | 137/DIG. 2 |

Primary Examiner—Alan Cohan
Assistant Examiner—Stephen M. Hepperle
Attorney, Agent, or Firm—Lyon & Lyon

[57] ABSTRACT

A device including a valving mechanism which can be operated by one hand, the device includes a housing which surrounds a resilient block of material. The housing may be squeezed to depress and deform the resilient block. Passageways extend through the resilient block to conduct liquid therethrough. A first passage includes a solid valve positioned therein. Compression of the resilient block causes displacement of the valve and distortion of the block material to break the seal around the valve. Additional material is provided strategically in this first passage to insure against leaks from system overpressure. A second passage includes a capillary to allow continuous low volume flow not controlled by an operator.

8 Claims, 5 Drawing Figures

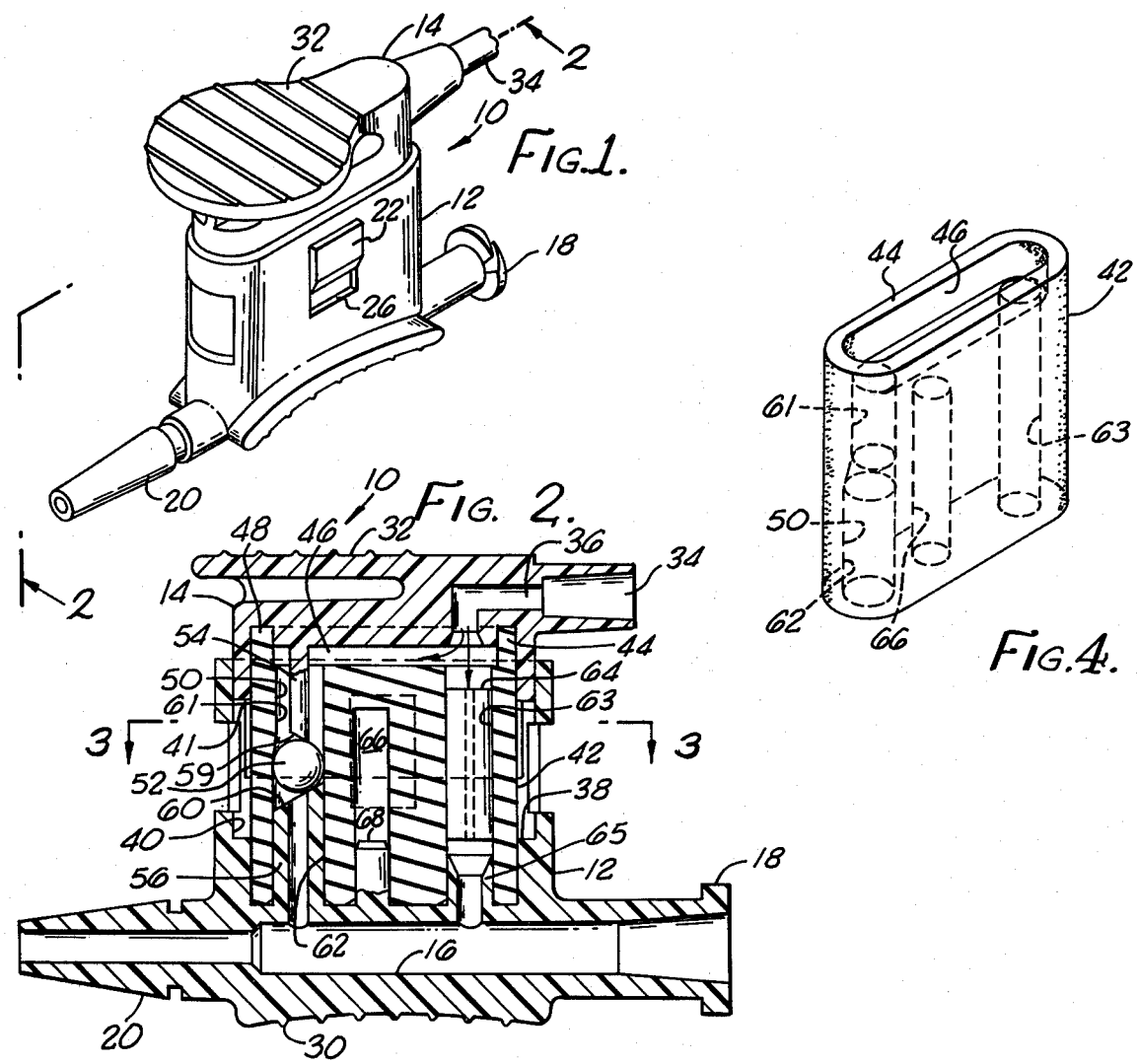
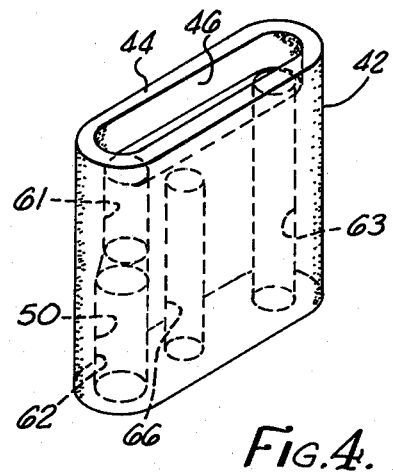
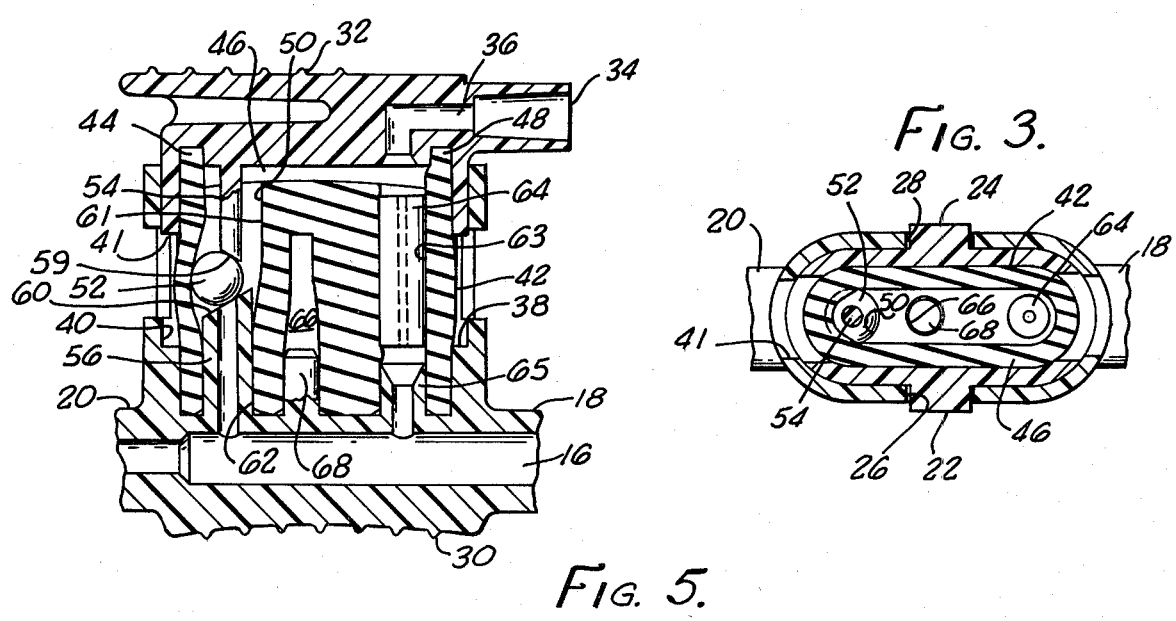

FLOW CONTROL APPARATUS

BACKGROUND OF THE INVENTION

The field of the present invention is flow control devices and particularly such devices as are employed with intravenous catheters.

With the advent of sophisticated monitoring equipment, it has become common practice in hospitals and particularly in intensive care facilities to maintain a continuous monitoring of certain body functions. This monitoring often includes intravenous sensing requiring a hollow catheter. The advantages of continuous monitoring of blood pressure and the like using such a hollow catheter have made this practice routine. However, such catheters are subject to blinding by blood clotting over the end in the vein or artery. A relatively successful solution to such blinding has been devised which includes a small medical fluid flow through the catheter. To this end, capillary tubes have been employed. The capillary flow is, however, only a partial solution to the problem. Use of such a system requires a compromise between excessive volumes of flow into the body and insufficient flow to assure against blinding.

To prevent excessive flow into the body and yet provide some means for overcoming clotting, an additional solution has been employed. A manually controlled high volume flow sufficient to insure against blinding of the catheter is used. The high volume flow is also useful for initially filling the catheter line with fluid, for removing air bubbles and the like. Such devices incorporating this bi-flow concept include U.S. Pat. No. 3,675,891 entitled "Continuous Catheter Flushing Apparatus" to Reynolds, et al and U.S. Pat. No. 4,192,303 entitled "Flow Restricting Device for Artificial Catheter Systems" to Young et al. The Reynolds et al and Young et al patents are incorporated herein by reference as indicative of the prior state of the art and to provide further illustration of utility of the present invention.

In overcoming difficulties in durability and convenience of use, a device has been developed which is disclosed in U.S. patent application Ser. No. 312,856, filed Oct. 16, 1981, to Sullivan, entitled "Flow Control Apparatus", the disclosure of which is incorporated herein by reference. The disclosed device includes a resilient block of material with at least one passage therethrough. This block is incorporated in a housing having a hollow body and a plunger. The plunger is also hollow, is slidably positioned in the hollow body and extends therefrom such that by compressing the hollow body and the plunger together, the resilient block is compressed and the passage therein deformed. The passage includes a ball therein which acts as a valve. The deformation of the passage is designed to allow fast flow past the valve.

The Sullivan device was designed to promote deformation of the resilient block solely through compression on the ends thereof. The resulting lateral deformation was generally random as the movement of resilient material around the passage could not be controlled by the operator through simple compression of the device. As particular movement could not be assured, the fit between the valve and the resilient block could not be in substantial interference. However, to insure against valve leakage, some interference fit between the valve and the passage was required. Consequently, a very narrow range of fit between the valve and the resilient block was required in the Sullivan device to gain reasonable reliability. Demanding tolerances and complicated or extensive reliability testing can create production and cost difficulties.

SUMMARY OF THE INVENTION

The present invention is directed to a flow control apparatus. The apparatus generally incorporated with the present invention includes a resilient block of material having a passage therethrough. This block of material is positioned in a housing having a hollow body and a hollow plunger which are partially telescoped together around the block. A valve member is incorporated in the passage. According to one aspect of the present invention, the valve member may be mechanically forced into an open position and the passage deformed to allow flow through the passage by compression of the hollow body and the plunger together. In another aspect of the present invention, the passage is constructed to provide both sufficient flexibility for easy deformation at the valve and yet prevent leakage due to upstream pressure.

The flow control apparatus of the present invention is a successor to the aforementioned Sullivan device, similarly overcoming the difficulties in reliability and use of earlier prior art. Furthermore, the present invention overcomes and circumvents the disadvantages of valve performance and manufacture resulting from the exacting requirements of the earlier Sullivan device.

Accordingly, it is an object of the present invention to provide an improved flow control mechanism and particularly a mechanism employed with intravenous catheters. Other and further objects and advantages will appear hereinafter.

BRIEF DESCRIPTION OF THE DRAWINGS

FIG. 1 is a perspective view of an assembled device of the present invention.

FIG. 2 is a cross-sectional elevation taken along line 2—2 of FIG. 1.

FIG. 3 is a cross-sectional plan taken along line 3—3 of FIG. 2.

FIG. 4 is a perspective view of a resilient block according to the present invention.

FIG. 5 is a cross-sectional elevation as in FIG. 2 with the resilient block in a deformed condition.

DETAILED DESCRIPTION OF THE PREFERRED EMBODIMENT

Turning in detail to the drawings, a preferred embodiment is illustrated as including a housing of rigid plastic material. The housing, generally designated 10 includes a hollow body 12 and a plunger 14. The hollow body 12 includes an upstanding generally ovular sidewall as best seen in FIG. 3. The hollow body 12 further includes a through passageway 16, integrally formed therewith, having a first end 18 and a second end 20 capable of accommodating conventional catheter tubing and fittings.

The plunger 14 also includes an ovular wall as can best be seen in FIG. 3. The wall of the plunger 14 is designed to fit in telescoping fashion within the ovular wall of the hollow body 12. Together, the interior of the hollow body 12 and the plunger 14 define an ovular cavity which can be varied in height by telescoping the plunger into and out of the hollow body 12. Naturally, other shapes may be defined by the housing 10 without departing from the present invention. Furthermore, the telescoping arrangement may be reversed in that the upper portion becomes the housing and the lower portion the plunger in telescoping arrangement.

To fix the two parts, the hollow body 12 and the plunger 14, together to both provide relative motion and prevent complete separation of the components, two tapered keepers 22 and 24 are integrally formed with the plunger 14. The keepers are tapered for easy snapping together of the hollow body 12 and the plunger 14 and yet retain the parts together by means of the upper flanges thereon. The keepers are positioned in slots 26 and 28 through the ovular wall of the hollow body 12. The slots 26 and 28 provide sufficient depth to accommodate squeezing of the housing in operation, as illustrated in FIG. 5.

The under surface 30 of the hollow body 12 and the upper surface of the plunger 32 are designed to give conventional manual purchase and are also sized to provide an easy grip for an average hand. The surfaces 30 and 32 may be roughened or provided with grooves such as illustrated in FIG. 1 to aid the operator in gripping the apparatus.

Located on the plunger 14 is an inlet 34 designed to accommodate conventional tubing or fittings employed with such devices. The inlet 34 includes a passageway 36 directed to the cavity in part defined by the plunger 14. Thus, medical fluids and the like can be admitted through the inlet 34 into the interior, or central cavity, of the housing 10. To further define the central cavity, the hollow body 12 includes an inward step or flange 38 having the same inside cross-sectional dimensions as the plunger 14. Thus, the cavity is defined both top and bottom with a common cross-section for careful location of the resilient block contained therein at these points. Yet, an annular space is allowed at 40 accommodating deformation of the resilient block. This space 40 also accommodates movement of the plunger as can be seen by comparing FIGS. 2 and 5. An additional space for resilient block deformation is also provided in the plunger 14 at 41.

The resilient block of material 42 contained within te central cavity of the housing 10 is shown independently in FIG. 4, in a relaxed state in FIG. 2, and in a compressed state in FIG. 5. This resilient material as employed in the preferred embodiment is a clear silicone rubber having a Shore hardness of A-25. A wide range of hardnesses may be employed with the block 42 which will affect the amount of force required to actuate the mechanism.

The block 42 is generally ovular in shape to fit closely within the interior of the plunger 14 and the inner flange 38. It includes an upstanding ovular flange 44 forming a continuous wall with the main block of material. This upstanding flange 44 defines a cavity 46 which serves as a manifold for directing medical fluid passing into the central cavity through the passageway 36. To accommodate this upstanding flange 44, the plunger 14 includes a groove 48 in the under surface thereof. The groove 48 is sized to closely fit the flange 44 for compression control when the housing 10 is squeezed. The groove 44 is not so deep as to allow the plunger 14 to completely fill the cavity of the manifold 46 defined within the flange 44.

The block of material 44 includes a first passage 50 conveniently extending through the block 42 from the manifold 46 to the other end of the block. This first passage 50 is incorporated in defining the valving mechanism of the flow control apparatus. Located within the first passage 50 is the valve member 52. In the preferred embodiment, the valve 52 is a ball having a diameter which is in interference fit with the relaxed inside diameter of the first passage 50. The ball may be of dimensionally stable plastic material. Under normal operation, the valve ball 52 provides a seal in the passage 50 such that no flow is experienced. This condition is illustrated in FIG. 2.

Associated with the hollow member 14 in substantial alignment with and extending into the first passage 50 is a first member 54. This first member 54 is smaller in cross-section than the passage 50 such that flow is unimpeded thereby. A second member 56 is associated with the hollow body 12 in alignment with and extending into the first passage 50. This second member 56 includes a central passageway 58 for flow therethrough. Again, flow is unimpeded through the passage 50 by this second member.

The members 54 and 56 extend into the passage 50 to the valve member 52. With the device in the relaxed state, the members 54 and 56 are not in interference with the valve member 52. This condition is illustrated in FIG. 2. When the housing is compressed, the members 54 and 56 do not interfere with the location of the valve as can best be seen in FIG. 5. To promote predictable movement of the valve member 52, the distal ends of the members 54 and 56 include end surfaces 59 and 60 which are other than perpendicular to the center line of the first passage 50. In the preferred embodiment illustrated, surfaces 59 and 60 are mutually divergent and are each generally plannar. This configuration predictably interferes with the valve member 52 to force it in a given direction laterally relative to the passage 50 under the force of compression of the housing 10. Thus, random distortion of the passageway and random location of the ball are avoided.

To avoid leakage in the first passage 50 by overpressure upstream of the valve member 52, the first passage 50 is divided into two sections. The first section 61 is located above the valve member 52. The passage is narrow in this section to provide additional material around the passage. The ball is positioned immediately below this area. Consequently, a maximum length of passage above the valve member 52, which is necessary subjected to the greater pressure, is further supported by additional material resulting from the smaller diameter passage. Immediately adjacent to and below the valve member 52 in the passage 50 there is a second section 62. Because of the interference of the valve member 52 to the flow, lower pressure is experienced downstream of the valve member 52 in this second section 62. Thus, flexibility is provided adjacent the valve member 52 such that the valve may be laterally displaced with comparative ease. Yet, additional strength is provided upstream of the valve to prevent overpressure from causing leakage in the valve.

A second passage 63 is provided conveniently through the resilient block 42 from the manifold 46 to the other end thereof. The second passage 63 is located at the opposite end of the manifold cavity 46 and has a capillary 64 located therein. The capillary 64 may be selected from any conventional capillary depending upon the amount of flow desired. Such capillaries are normally of glass and are rigid such that they cannot be deformed in the present application.

Located below the capillary is an upstanding tube 65 formed integrally with the hollow body 12. The tube 65 also forms part of the outlet, draining into the through passageway 16, the outer dimension of the tube 65 is substantially equal to the outer dimension of the capillary 64 to conveniently fit snuggly within the second passage 63. The tube 65 also acts to prevent the capillary from sliding into the through passageway 16.

Located intermediate the first and second passages 50 and 63 is a space 66. The space 66 is positioned adjacent the first passage to allow exaggerated deformation of the wall of the passage 50 when the resilient block 42 is compressed. This space 66 extends only partially through the block 42 to avoid flow therethrough. An upstanding pin 68 also formed integrally with the hollow body 12 acts to control the deformation of the wall of the passage 50 into the space 66 as can best be seen in FIG. 5.

Looking then to the operation of the preferred embodiment, the through passageway 16 may be conveniently placed via passageway end 18 in communication with monitoring equipment such as a transducer or a controlled source of fluid. The opposite end of the through passageway 16 is connected to the catheter or other distribution mechanism for the monitored liquid. The inlet 34 is coupled with a source of fluid which is to slowly flow into the catheter for inhibiting clotting at the end thereof. Under normal operation, medical fluid introduced through inlet 34 passes in a low volume flow through the capillary 64 and into the through passageway 16. When flushing of the system, or additional clearing of the catheter, is required, an operator may grip the housing 10 so as to squeeze the two parts, the hollow body 12 and the plunger 14, toward one another. As the housing is squeezed, the plunger, acting primarily on the upstanding flange 44 on the block 42, compresses the resilient material of the block 42 and distorts the passage 50 as illustrated in FIG. 5. The members 54 and 56 are brought into interference with the valve ball 52 and positively force it laterally against the side of the passage 50. Thus, a path is created through the passage 50 around the valve ball 52. Release of the housing 10 removes the compression force from the resilient block 42 allowing the device to return to its relaxed state. In doing so, the passage 50 closes around the valve 52 and seals the passage once again. The increased thickness of the material above the valve ball 52 acts in this shut-off mode to resist leakage due to overpressure in the upstream system.

Provided as an example only are the following dimensional relationships. The first passage 50 has a nominal diameter of 0.115 inches. The upper section is restricted as discussed above such that the inner surface of the passage 50 adjacent the end of the resilient block 42 is formed with a radius of 0.045 inches from the nominal center line which is then tapered outwardly at a 30° angle to the major center line of the resilient block 42 to intersect the larger diameter on either side of the reduced radius. The valve ball 52 has a nominal diameter of 0.150 inches. The resilient block is clear silicone rubber having a Shore hardness of A-25 and the ball is of acetal resin. The thickness of the wall of the block of resilient material 42 between the first passage 50 and the end of the block most adjacent that passage and below the location of the valve ball 52 is 0.0675 inches. The upper wall portion is increased by the reduced radius discussed above.

Thus, an improved flow control device capable of facile one-handed operation, easy fabrication and excellent reliability is disclosed. While embodiments and applications of this invention have been shown and described, it would be apparent to those skilled in the art that many more modifications are possible without departing from the inventive concepts herein. The invention, therefore, is not to be restricted except in spirit of the appended claims.

What is claimed is:

1. A flow control apparatus including a housing having a hollow body and a plunger slidably positioned in and extending from said hollow body, said housing including a central cavity defined by said hollow body and said plunger, an inlet into said central cavity and an outlet from said central cavity; a block of resilient material positioned in said central cavity between said inlet and said outlet and having a first passage therethrough oriented to provide communication between said inlet and said outlet; and a valve member in said passage, one of said hollow body and said plunger including a first member affixed thereto and extending into said first passage and the other of said hollow body and said plunger including a second member affixed thereto and in said first passage on the other side of said valve member from said first member, wherein the improvement comprises each first and second members being constructed and arranged to extend to and displace said valve member against one side of said first passage when said hollow body and said plunger are compressed toward one another against said resilient material.

2. The flow control apparatus of claim 1 wherein the improvement further comprises said first member including a distal end having an end surface at least a portion of which is other than perpendicular to the center line of said first passage.

3. The flow control apparatus of claim 2 wherein the improvement further comprises said second member extending into said first passage and including a second distal end having an end surface at least a portion of which is other than perpendicular to the center line of said first passage.

4. A flow control apparatus including a housing having a hollow body and a plunger slidably positioned in and extending from said hollow body, said housing including a central cavity defined by said hollow body and said plunger, an inlet into said central cavity and an outlet from said central cavity; a block of resilient material positioned in said central cavity between said inlet and said outlet and having a first passage therethrough oriented to provide communication between said inlet and said outlet; and a valve member in said passage, said hollow body including a first member affixed thereto and extending into said first passage and said plunger including a second member fixed thereto and extending into said first passage on the other side of said valve from said first member, wherein the improvement comprises said first and second members being constructed and arranged to extend to and displace said valve member against one side of said first passage when said hollow body and said plunger are compressed toward one another against said resilient material, said first member including a distal end having a first end surface which is other than perpendicular to the center line of said first passage and said second member including a distal end having a second end surface which is other than perpendicular to the center line of said first passage, said first and second end surfaces being oriented such that they are mutually divergent.

5. The flow control apparatus of claim 1, 2, 3 or 4 wherein said valve member is a ball having a diameter in interference fit with the inside diameter of said first passage.

6. A flow control apparatus comprising in combination a housing having a hollow body and a plunger slidably positioned in and extending from said hollow body, said housing including a central cavity defined by said hollow body and said plunger, an inlet into said central cavity and an outlet from said central cavity;

a block resilient material positioned in said central cavity between said inlet and said outlet and having a first passage therethrough oriented to provide communication between said inlet and said outlet; and a valve member in said first passage, said valve member being a ball having a diameter in interference fit with the inside diameter of said first passage, one of said hollow body and said plunger including a first member fixed thereto and extending into said first passage to said valve member and the other of said hollow body and said plunger including a second member fixed thereto and in said first passage on the other side of said valve member from said first member, said first and second members being constructed and arranged to extend to and displace said valve member against one side of said first passage when said hollow body and said plunger are compressed toward one another against said resilient material, said first member including a distal end having an end surface which is other than perpendicular to the center line of said first passage.

7. A flow control apparatus comprising in combination a housing having a hollow body and a plunger slidably positioned in and extending from said hollow body, said housing including a central cavity defined by said hollow body and said plunger, an inlet into said central cavity and an outlet from said central cavity;

a block of resilient material positioned in said central cavity between said inlet and said outlet and having a first passage therethrough oriented to provide communication between said inlet and said outlet; and a valve member in said passage, one of said hollow body and said plunger including a first member fixed thereto and extending into said first passage to said valve and the other of said hollow body and said plunger including a second member affixed thereto and in said first passage on the other side of said valve member from said first member, said first and second members being constructed and arranged to extend to and displace said valve member against one side of said first passage when said hollow body and said plunger are compressed toward one another against said resilient material, said first passage being adjacent a surface of said block of resilient material defining a wall therebetween, said wall being relatively thicker immediately upstream of said valve member than adjacent to and downstream of said valve member.

8. The apparatus of claim 1 wherein said first passage includes a first section and a second section, said first section of said first passage being narrower than said second section, said first and second members retaining said valve member in said second section adjacent one end of said first section, said first section being adjacent and thereby defining said thicker portion of said wall.

* * * * *

UNITED STATES PATENT AND TRADEMARK OFFICE
CERTIFICATE OF CORRECTION

PATENT NO. : 4,456,223
DATED : June 26, 1984
INVENTOR(S) : WENDELL V. EBLING

It is certified that error appears in the above—identified patent and that said Letters Patent is hereby corrected as shown below:

In column 7, line 14, after block, add -- of --.

Signed and Sealed this

Fourth Day of December 1984

[SEAL]

Attest:

GERALD J. MOSSINGHOFF

Attesting Officer    Commissioner of Patents and Trademarks